United States Patent [19]

Berthold et al.

[11] 4,390,274

[45] Jun. 28, 1983

[54] USE OF A METHOD, PARTICULARLY AN AUTOMATIC METHOD, FOR MEASURING LIGHT AS WELL AS IMPROVEMENTS AND APPARATUSES FOR CARRYING OUT THE SAME

[76] Inventors: Fritz Berthold, Engelsbranderstrasse 12, 754 Neuenbürg, Fed. Rep. of Germany; Seppo Kolehmainen, Ganzenstraat 11, Zolder, Belgium; Veikko Tarkkanen, Breulsweg 1, Wijlre, Netherlands

[21] Appl. No.: 111,000

[22] Filed: Jan. 10, 1980

[30] Foreign Application Priority Data

Jan. 18, 1979 [DE] Fed. Rep. of Germany ....... 2901919

[51] Int. Cl.$^3$ .................. G01N 1/00; G01N 21/00; C12Q 1/66
[52] U.S. Cl. .................................. 356/36; 435/8; 356/436
[58] Field of Search ............... 422/52, 62, 68; 356/39, 356/40, 339, 432, 436, 36; 435/8

[56] References Cited

U.S. PATENT DOCUMENTS

| | | | |
|---|---|---|---|
| 3,719,410 | 3/1973 | Kallet | 356/36 |
| 3,745,090 | 7/1973 | Chappelle et al. | 435/8 |
| 3,797,999 | 3/1974 | Wiiz et al. | 422/52 |
| 3,841,765 | 10/1974 | Lambert et al. | 356/246 |
| 3,869,215 | 3/1975 | Nolan | 356/246 |
| 3,882,028 | 5/1975 | Zolner | 250/361 |
| 4,058,732 | 11/1977 | Wieder | 250/461 B |
| 4,101,276 | 7/1978 | Anderson | 356/39 X |

OTHER PUBLICATIONS

Lumit Application 507, "Internal Standardization", Lumac Systems AG, 1977.
Lundin, A. et al., "Sensitive Measurement of Flash Induced Photophosphorylation in Bacterial Chromatophores by Firefly Luciferase", FEBS Letters, pp. 73-76, vol. 79, No. 1, Jul. 1977.
Lumacounter ®, Model 2080, specification and description flyers, Lumac Systems A.G.
Celltester Model 1030, specification and description flyer, Lumac Systems, AG., 1978.

Primary Examiner—John K. Corbin
Assistant Examiner—Bruce Y. Arnold
Attorney, Agent, or Firm—Spencer & Kaye

[57] ABSTRACT

A method for photometrically measuring a reaction process at a darkened measuring station which contains a sample having an unknown quantity of a substance which acts as a reaction partner with a reagent. The sample is provided with a first reagent which acts as a reaction partner with a reaction partner present in the sample. A first photometric measurement of the sample is taken at the darkened measuring station to measure the reaction process between the first reagent and the reaction partner in the sample, and this first measurement is used for computation. At least one additional reagent which differs from the first reagent and which constitutes a further reaction partner is added to the sample at the darkened measuring station after the first photometric measurement. A photometric measurement of the sample is conducted after the addition of each additional reagent and during the course of a reaction between reaction partners then present. The unknown quantity of the substance in the sample is determined from all the measured values. The first reagent can be added to the sample prior to transferring the sample to the darkened measuring station or can be added to the sample at the darkened measuring station.

38 Claims, 8 Drawing Figures

USE OF A METHOD, PARTICULARLY AN AUTOMATIC METHOD, FOR MEASURING LIGHT AS WELL AS IMPROVEMENTS AND APPARATUSES FOR CARRYING OUT THE SAME

BACKGROUND OF THE INVENTION

The invention relates to a method, particularly an automatic method, for measuring light, in which at a darkened measuring station a series of consecutively supplied samples are each supplied with a reagent, the reaction process is measured photometrically and the measuring result is further processed according to a computer program.

The invention also relates to an apparatus for carrying out this method and comprising a measuring station located in a darkened measuring chamber, a transfer section passing through the measuring chamber for supplying and removing successive discrete samples, a reagent supply system leading into the measuring chamber to supply the sample located in the measuring station, a light detector and a computing and evaluating device.

Methods and apparatus of this type are known in connection with the devices called LUMACOUNTER, Type 2080, and Celltester, Type 1030, which are sold by the firm LUMAC SYSTEMS AG, Reichensteinerstrasse 14, CH-4000 Basle 2 Switzerland.

In such a prior art device, a certain reagent is fed to the sample after the sample has been transferred to the darkened measuring station. It is also possible to inject the same reagent several times at the darkened measuring station. This device deviates from the usual practice of adding the reagent to the sample while the latter is still outside the darkened measuring station and then moving the sample to the darkened measuring station. If, however, with prior art devices of this type, several measurements must be made in succession with the successive addition of different reagents, it is necessary, after the first reagent has been added at the darkened measuring station, to remove the sample to the open air to add the next reagent whereupon the sample, together with the added reagent, is returned to the darkened measuring station; the reason is that the prior art devices of this type are not equipped for the addition of different reagents to a sample which remains at the darkened measuring station.

The prior art device of this type can be operated either fully automatically or semi-automatically, or also manually by a technician; this also applies within the scope of the invention in which the automatic, and especially the fully automatic mode of operation is preferred.

If, during successive measurements with successively added reagents, the sample is transferred from the darkened measuring station to the open air for the purpose of adding the next reagent, this may result in measuring errors due to the phosphorescence or fluorescence being superposed by the incidence of extraneous light. Within the scope of the invention, such measuring errors are considered to be more critical than superposition of fluorescence or phosphorescence which occurred when the original sample was exposed to light. This is because the resultant luminous background of the measurement averages out sooner in successive measurements of the same sample with the successive addition of different reagents, than a superposed fluorescence or phosphorescence which appears for the first time only after the first measurement.

SUMMARY OF THE INVENTION

It is therefore the object of the invention to avoid, in light measurements of samples at a darkened measuring station, interference effects which may occur if the sample is returned from the darkened measuring station into the light.

For this purpose, the present invention provides a method wherein multiple measurements of each sample are taken, including the steps of photometrically measuring at the darkened measuring station during a first measuring period the reaction of reaction partners, at least one of which is different from a particular reagent and was added to the sample before its transfer to the darkened measuring station, then adding the particular reagent at the darkened measuring station, then photometrically measuring, still at the darkened measuring station, during a second measuring period the reaction of the original reaction partners with the reagent added at the darkened measuring station, and determining from the measured values of both measuring periods, according to a computer program, the quantity of an unknown reaction partner in the combination of sample and reagent.

Thus, instead of adding, as in the prior art process, first one reagent at the darkened measuring station and then adding the second reagent after again having taken the sample out of the darkened measuring station into the open air, the invention reverses the sequence of these steps by adding the first reagent to the sample before the sample is brought to the darkened measuring station and by then adding the second reagent to the sample without taking the sample out of the darkened measuring station.

A further advantage of this method is that any other interference, such as uncontrolled temperature disturbances, which result from taking the sample out and returning it to the measuring station, are kept small.

The method according to the invention is of particular significance in the case where it is used for internal standardization of each sample (see FEBS LETTERS, Volume 79, Number 1, July, 1977, North Holland Publishing Company, pages 73 to 76, the article entitled, "Sensitive Measurement of Flash-Induced Photophosphorylation in Bacterial Chromatophores by Firefly Luciferase" by Lundin, Thore and Baltscheffsky, in particular, page 74, first complete paragraph, last sentence).

In such an application, the method according to the invention provides that at the darkened measuring station an internal standard is added to the sample as a reagent and that the quantity of the unknown original reaction partner is determined from the measured values of both measuring periods, the first one of which corresponds to the luminescence reagent added before the sample was moved to the darkened measuring station.

While the two aforementioned applications of the prior art process can still be carried out with a prior art device in which only one reagent can be added at the darkened measuring station, the invention constitutes an advantageous improvement in which more interference effects are eliminated. Thus, when different reagents are added, several of these can be added at the darkened measuring station. Further, it is possible to add a first reagent to the sample even before the latter is moved to the darkened measuring station. In many applications, however, all of the reagents are added to the sample at the darkened measuring station.

The method according to the invention, or the novel use of the known method, respectively, is of particular significance for measuring bioluminescence (see Waldemar Adam's "Biologisches Licht" [Biological Light] in the journal "Chemie in unserer Zeit" [Chemistry of our Time], Volume 7, 1973, Number 6, pages 182 to 191). They are also applicable, however, to other light measurements such as the measurement of chemiluminescence, the measurement of fluorescence or the measurement of light absorption. Yet another application is, for example, nephelometry, the measurement of scattered light. Roughly speaking, a distinction can thus be made between photometry with an external light source, on the one hand, and photometry based on internal effects in the sample.

Particularly important areas of use for the present invention include determination, by bioluminescence, of ATP, preferably by firefly luminescence, PAPS, preferably by sea-anemone bioluminescence, Ca, preferably by jellyfish bioluminescence, or $FMNH_2$, NADH or NADPH. Further, substrates which can be determined by bioluminescence include tRNA, creatine, glycerin, glucose-6P, GTP, cAMP by the ATP assay method, or the number of cells of somatic or microbial origin or the physiological activity of cells by measuring ATP, ADP and AMP, ethanol, D-glucose-6-P, alpha ketoglutarate, glutathione, D-lactate, and pyruvate by coupling of NADH or NADPH to a bacterial bioluminescene system.

The simultaneous determination of ATP, ADP and AMP is possible. It is further possible to determine creatine kinase (CK), other kinases and other enzymes which produce or consume ATP, dehydrogenases such as glucose dehydrogenase and other enzymes which produce or consume NADH or NADPH and oxidases, catalases or peroxidases which produce or consume peroxides or superoxides.

$H_2O_2$ or superoxide can be measured by bioluminescence means, preferably Latia or Pholas mussel bioluminescence, or polychaeta worm bioluminescence, or by chemiluminescence, such as with luminol, lucigenin or pyrogallol.

Chemiluminescence can be used to determine cholesterol, D-glucose, and uric acid, with $H_2O_2$ consumption.

Fluorescence methods can be used to determine NADH, NADPH, DNA, RNA, amino acids, fluorescence, 4-methyl-umbelliferone, rhodamine, and other molecules which, after having been excited with light of a certain wavelength, are capable of re-emitting light on a different wavelength.

Light absorption methods can be used to determine substances which absorb light of a certain wavelength, such as NADH, NADPH, or colored substances, or complexes with added reagents such as phosphates in ammonium, molybdophosphate, hydrogen peroxide with diamine benzidine tetrahydrochloride or phosphatase enzymes with 4-nitrophenol.

The method according to the invention, in which several different reagents are added to the sample in succession at the darkened measuring station without intermediate transfer of the sample into the open, is of very special significance when the reaction of the second reaction partner, for example of an internal standard, decays very rapidly. In this case the invention even solves the problem, not yet solved in the comparable luminescence measuring art, of being able to measure very rapidly decaying second reactions of a sample to which a first reagent had already been added. This is the case also in some luminescence reagent reactions particularly if LUMINOL is used, and for light absorption measurement. The prior art methods were unsuitable from the start for such measurements.

However, the invention is limited neither to measuring very short reaction times associated with liminescence nor to internal standardization. Rather, the invention provides quite generally an increased measuring accuracy by reducing the effects of external sources of interference, such as phosphorescence or fluorescence due to unintentional or uncontrolled incidence of extraneous light and nonstatic conditions such as, in particular, nonconstant temperature conditions. Accordingly, at the darkened measuring station, the sample is advantageously kept at a constant temperature in order to provide uniform measuring conditions at least during the measuring phases, in spite of the successive addition of reagents which must also be brought to the temperature level of the sample.

An example, in which the primary consideration is neither short reaction times nor internal standardization, is the possibility of measuring leucocytes for immunology tests. For this purpose, one can add, for example, luminol to the sample as a luminescence reagent before the first measurement outside the darkened measuring station, so as to be able to use the first measurement to perform an initial type of background measurement, that is measurements of blank values of nonspecific reactions with the sample. At the measuring station, a stimulant is then added as the second reagent, for example concavalin A. This second reagent stimulates the cells into chemiluminescence which is the actual object of the measurement as contrasted to the previously determined background. While this measurement can still be performed as broadly defined in order to subsequently quantitatively measure the substance to be determined by means of chemiluminescence, the addition of an internal standard as described herein, is required.

In the case of internal standardization, a known quantity of the same substance, whose unknown quantity is to be measured in the sample is always added as the standard. Of primary importance here as regards technique of application is the measurement of ATP, adenosine triphosphate. The internal standard to be added is then a known quantity of ATP so as to find the unknown quantity in the sample. ATP is a substance which, in simple terms, stores energy within the cell which can be released on demand by a stimulant (with reference to ATP measurements, see also U.S. Pat. No. 3,745,090).

Typical examples of the application of ATP measurements without the use of extraction agents or stimulants are in measurements of hemolytic blood damage, release of very low concentrations of ATP in the case of a myocardial infarction or, a frequent occurrence, bacterial cell damage due to antibiotics. In these cases, free ATP is present in the blood sample.

If, on the other hand, the total ATP content in a sample is to be measured, or measurements are taken at cells of samples in which the cells are not yet damaged, the ATP still present in the cell has to be stimulated to cause it to pass through the cell wall, or it must be extracted through the cell wall, to then be able to interact with a luminescence reagent with the emission of light. This extraction or stimulation is effected by means of a so-called "nucleotide releasing reagent." If, furthermore, free ATP was measured in a first measurement, the original proportion of ATP inside the cells can also be measured by means of a subsequent measurement after adding such an extraction agent or stimulant, and if appropriate, an internal standardization can be performed in a third measuring phase, referring to the second measurement, by adding a known quantity of ATP.

Another typical case of multiple measurements after adding different reagents to a sample which remains at the darkened measuring station is the simultaneous determination of ATP, ADP (adenosine diphosphate) and AMP (adenosine monophosphate).

In this connection, a further example of a rapid reaction decay of luminescense is the hydrolysis of ATP from thrombocytes by means of stimulants, for example thrombin, ADP, collagen or adrenalin.

A particularly important aspect of the invention, is that in a measuring phase which can generally be assumed to be the first phase, a reaction is measured which is the result of a "releasing agent" having been added to the sample at the darkened measuring station, thus triggering the passage of, for example, ATP through the cell walls of an organic substance and making the intended measurement possible. This measurement can then be performed in the second measuring run at the darkened measuring station after adding a further reagent at the darkened measuring station again followed in a third measuring process, after the addition of an internal standard at the darkened measuring station, by a third measurement. All this was impossible with the prior art methods and devices without exposing the sample, between measurements, again and again to the open atmosphere.

In this connection it is important that the reagent be added to the sample at the darkened measuring station in such a manner that a representative measurement becomes possible and, in particular, the reagent and the sample are well mixed together. This is accomplished with the type of equipment involved by the design of appropriate devices for injecting the reagent into the sample and must likewise be maintained, within the scope of the invention, if several means for supplying the sample are arranged inside the darkened measuring chamber. If necessary, the sample must be mixed thoroughly at the darkened measuring station before and/or between the individual measuring phases by means of devices which are separate from the supplying means, such as, for example, a shaking or stirring device.

DESCRIPTION OF THE PREFERRED EMBODIMENTS

Figure 1:
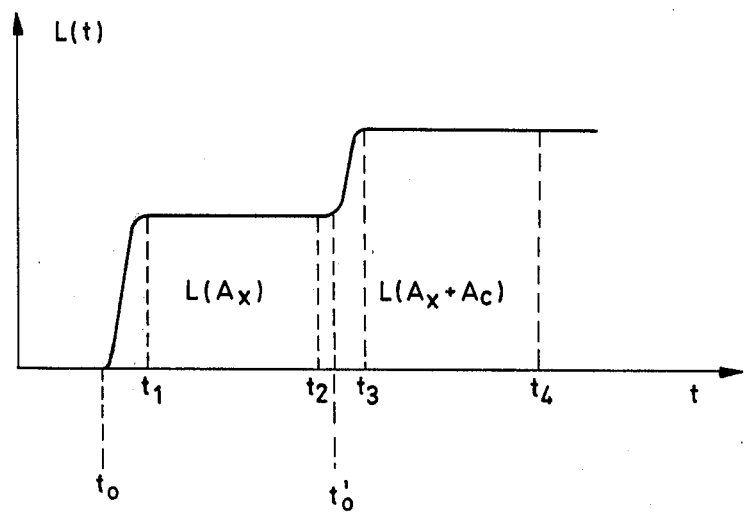
FIG. 1 shows a time curve for an ATP measurement with purified reagents.

A reaction during which light is generated can be represented schematically as follows:

$$A + LR = L(A).$$

The value to be measured is the unknown quantity $A_x$ of substance A which is responsible for the emission of light, but only in connection with a particular, different reaction partner LR (luminescence reagent). Within certain limits, the light yield $L = \Sigma h\nu$ is proportional to the quantity A, that is to say $L = kA$.

It is here not necessary to stipulate that there be a proportional relationship between A and L; it is sufficient if L is a known function of A or one which is to be determined by another measurement.

The factor k is not always constant. There are interfering influences due to chemical admixtures or other parameters such as temperature, turbidity and color, which cause the light yield to be reduced with respect to optimum conditions. By definition, the factor k under optimum conditions is set to be $k_o$.

Borrowing from the terminology of liquid scintillation counting, these effects can be called extinction. There are then two different types of extinction: color extinction and chemical extinction.

With color extinction, the emitted light is absorbed or diffused in the sample itself, due to its coloring or turbidity, in such a manner that it no longer reaches the light detector.

With chemical extinction, there is no light emission at all since, due to interference effects, the excited molecules release their energy without radiation.

In both cases the light yield is reduced with respect to optimum conditions: $k < k_o$.

The following method for the quantitative determination of A is disclosed in Lumit Application 507 by Lumac Systems AG, Basel, 1977: a duplicate of the sample is prepared, maintaining identical conditions as for the sample preparation so that both samples contain the same unknown quantity $A_x$.

A known quantity $A_c$ of the light-generating substance is added manually to the second sample (duplicate).

Based on the addition of the same quantity of the reagent LR, the following light yields are obtained (in relative units):

$$L(A_x) = kA_x \qquad (1)$$

$$L(A_x + A_c) = k(A_x + A_c) \qquad (2)$$

assuming the same factor k for both samples, a condition which is not always fulfilled in practice. Eliminating k, this gives:

$$A_x = A_c \frac{L(A_x)}{L(A_x + A_c) - L(A_x)} \qquad (3)$$

Equation (3) yields $A_x$ in the same units as $A_c$, for example in pg.

However, this prior art method is very cumbersome since it requires a series of manipulations and calculations. In practice it is performed manually and, above all, the same sample must be measured twice, resulting in doubled consumption of reagent. Therefore, in routine operation, this calibration is frequently not performed so that the results contain corresponding inaccuracies.

The invention makes it possible to modify this method, and to at least partially automate it, in such a manner that high accuracy is achieved even in routine operation. Simultaneously, the use of reagents can be reduced.

According to the invention, the following process steps can be carried out automatically:

1. The sample with the unknown quantity $A_x$ is placed into the light-proof measuring chamber in front of the light detector (for example, photodiode, photomultiplier).

2. A certain quantity of the reagent LR is added.

As an alternative to steps 1 and 2, it is also possible, under certain circumstances, to interchange steps 1 and 2, i.e., to first fill in the reagent LR and then put the sample into the light-proof chamber.

3. The amount of light $L(A_x)$ produced when the sample and LR meet is measured over a certain period of time, typical values being between 5 and 60 seconds. The light quantity can be integrated, for example, or the maximum emission of light is determined (see FIGS. 1 and 2).

4. Now the known quantity $A_c$ is added (injected).

Figure 2:
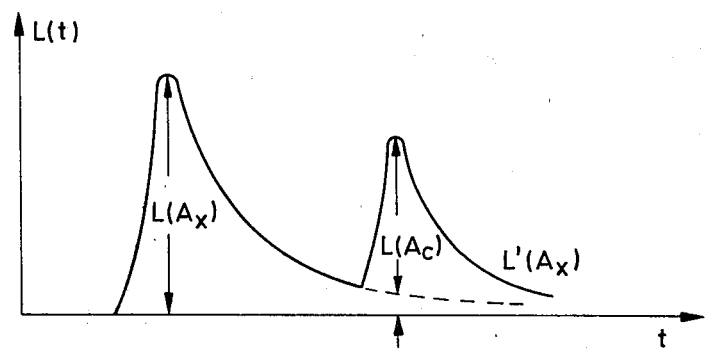
FIG. 2 shows a time curve for a kinetically fast system.

5. The light quantity $L(A_x+A_c)$ is measured corresponding to the measurement of $L(A_x)$. FIG. 2 provides a variant for impure chemicals or reaction systems with fast kinetics, example LUMINOL, or photobacteria.

6. The calculation according to equation 3 is performed automatically and produces the final result $A_x$. If there is a curve as shown in FIG. 2, the value $L'(A_x)$ must be determined first instead of $L(A_x)$ and must then be inserted into equation (3).

In the apparatus embodiments of the present invention, a distinction should be made between measuring individual samples and automatically measuring many samples. Automatic extinction correction by way of automatic standardization is of advantage in both cases.

Figure 3:
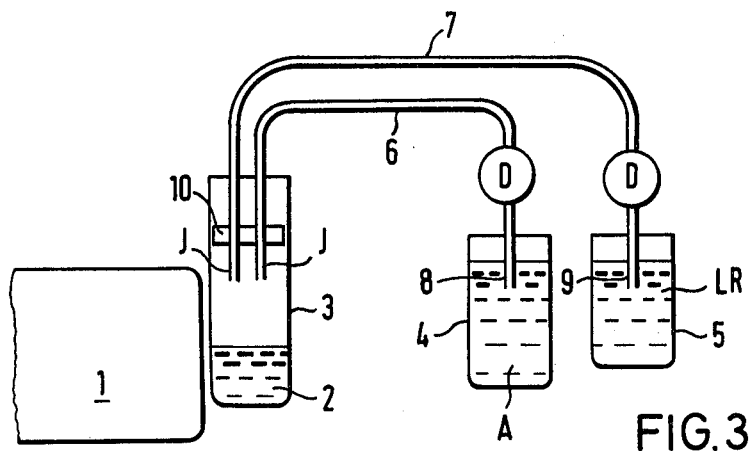
FIG. 3 shows an elementary arrangement employing automatic standardization.

A practical embodiment is shown in FIG. 3. Here the sample can be introduced into the light-proof measuring cell, and the LR, for example LUCIFERIN-LUCIFERASE reagents and the like, can be injected at the darkened measuring station, using means, for example, some of which are disclosed in German Offenlegungschrift No. 2,728,965 for supplying reagents at a non-darkened measuring station.

The light detector is, for example, a photodiode or a photomultiplier.

For automatic measurements according to the invention, the above-mentioned sequence also has the following alternative, which is similar to the manual method but does not lead to the saving of half the quantity of sample and reagent fluid as made possible within the scope of this invention.

1. A duplicate is made of each sample. This applies both to discrete analyzers (each sample is located in its own vessel) and to continuous flow analyzers (TECHNICON), all samples being located in a tube and separated only by the carrier liquid and, possibly, by air bubbles. 2. Sample pipette and duplicate are placed into consecutive positions of the conveying system (for example, a chain or magazine), or are introduced into consecutive positions in the continuous flow system.

3. The calibrating quantity $A_c$ is automatically added to the duplicate sample.

4. $L(A_x)$ and $L(A_x+A_c)$ of sample and duplicate are measured and $A_x$ is determined in accordance with equation (3).

This second method is applied if (a) impure chemicals are used and the determination of $L'(A_x)$, according to FIG. 2, becomes inaccurate;

(b) LR also changes or is spent by the time $A_c$ is added.

The equipment can be controlled and the results can be calculated with particular advantage using microprocessors.

The substance A to be determined could be ATP, for example, in this case the LR would be luciferin/luciferase.

The invention will now be explained in greater detail with the aid of the drawings.

FIG. 1 shows the time curve $L(t)$ of the intensity of luminescence for measuring ATP with purified reagents. At time $t_0$, the sample and LR are mixed, at time $t_0'$ $A_c$ is added. The differences in time $t_2-t_1$ and $t_4-t_3$ designate the measuring phases.

Preferably, an integration function is used. After LR has been added there is a brief waiting period until thorough mixing has been achieved, then the area from $t_1$ to $t_2$ is integrated. Correspondingly, after $A_c$ has been added, the area from $t_3$ to $t_4$ is integrated, where $t_4-t_3=t_2-t_1$.

Since the total volume of the reagents and of the sample is increased by adding a standard, the step of $L(A_c+A)$ is not absolutely proportional to the added amount of $A_c$ or proportional to the concentration of $A_c+A_x$ in the new volume.

The values of $t_4-t_3$ are corrected by means of a programmed computer, with respect to a change in concentration.

FIG. 2 shows the time curve for a kinetically fast system.

After mixing, the emission of light drops rapidly. The preferred method used is the "peak method" in which the maximum value of the light emission rate is measured. When determining $L(A_c)$, the background originating from the first peak must be taken into consideration (dashed line). It is preferably extrapolated from the drop of $L(A_x)$ with time before the addition of $A_c$.

In the arrangement for automatic standardization according to FIG. 3, a light detector 1, for example a photomultiplier, is arranged at the darkened measuring station to which a liquid sample 2 has been brought inside a sample vial 3.

A calibrating reagent A, for example ATP, is disposed in a first reservoir container 4. A second reservoir container 5 contains a luminescence reagent LR, for example luciferin/luciferase. Dispensers D can successively suck up A and LR through respective hose connections 6 and 7 which are provided with suction heads 8 and 9, to be mixed in measured quantities with the sample 2 by means of an injector I which, for example, has the shape of a needle, and is held by a plug 10 inserted into the sample vial 3. At least one reservoir container, for example one bottle each, must be provided for each reagent. In an alternate embodiment, a single injector with one-way valve branching to the different reservoir containers and/or, if necessary, even a single dispenser with two alternative supply lines can be used (see also FIGS. 6 to 8).

Figure 4:
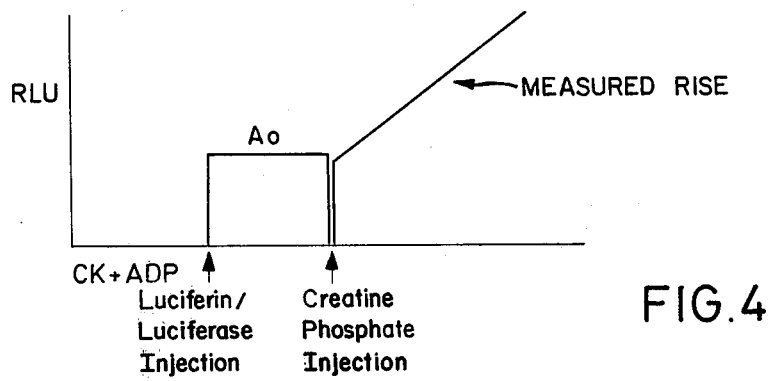
FIG. 4 shows a time curve for a chemical analysis with multiple injection of different types of reagents at the darkened measuring station.

FIG. 4 shows a measuring curve for the relative light unit RLU over time, as it occurs in enzyme measurements.

Thus multiple injection systems according to the invention can be used for chemical analyses for which several reagents must be added in sequence, for example an enzymatic analysis for creating kinase (CK) which appears in the blood, for example, in a heart attack and in connection with other muscular damage: A reaction as follows is set up:

$$\text{creatine phosphate} + \text{ADP} \xrightarrow{CK} \text{ATP} + \text{creatine}.$$

This analysis can be performed with a multiple injection system according to the invention, as follows:

(a) A sample of creatine kinase and ADP is pipetted into a cuvette and placed into a light-proof measuring chamber.

(b) A luciferin/luciferase reagent is injected into the mixture of CK and ADP in a cuvette located in the measuring chamber. This produces the 0 value of ATP in the ADP reagent ($A_0$) (FIG. 4).

(c) Creatine phosphate is injected through a tip at the injection head and the ATP production rate including that generated during the previous reaction is measured during a period of 0.5 to 10 minutes, preferably 1 to 3 minutes, in order to determine the ATP production rate which corresponds to the activity of CK in the sample.

Figure 5:
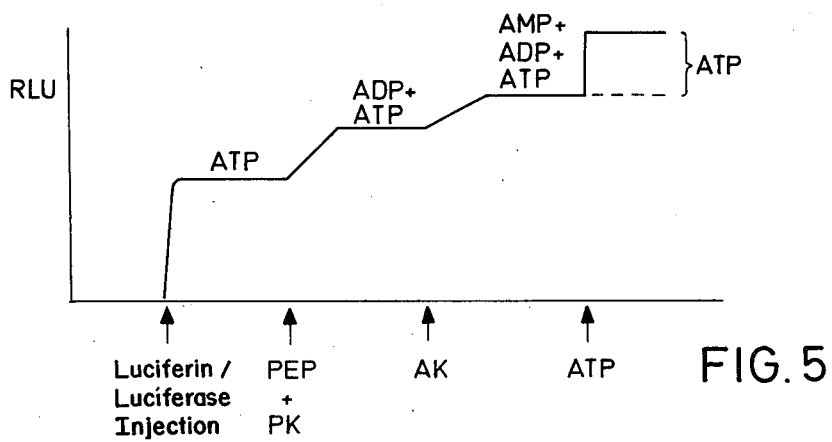
FIG. 5 shows a time curve for measuring several substrates in the same sample, particularly ATP, ADP and AMP with multiple injection of different types of reagents.

Turning now to the embodiment shown in FIG. 5, a determination is made of a sample which contains ATP, ADP and AMP according to the following technique:

(a) A luciferin/luciferase reagent is injected into the sample. The development of ATP is then monitored and measured at the darkened measuring chamber. The reaction between the luciferin/luciferase reagent and ATP produces a constant light emission (zero order rate) which is shown in FIG. 5 at "ATP".

(b) A mixture of phosphoenol pyruvate (PEP)-+pyruvate kinase (PK) is injected, as shown in FIG. 5. The development of ATP is monitored until a zero order increase takes place. This value is characteristic for ATP+ADP. The reaction is as follows:

$$\text{ADP} + \text{PEP} \xrightarrow{PK} \text{ATP} + \text{pyruvate}.$$

(c) Then adenylate kinase (AK) is injected into the sample, which converts the AMP into ATP:

$$\text{AMP} + \text{ATP} \xrightarrow{AK} 2\text{ADP} + 2\text{PEP} \xrightarrow{PK} 2\text{ATP}.$$

(d) Finally, a certain amount of ATP is injected in order to generate the internal standardization values. This method makes the measurement reproducible and fast and saves considerable amounts of reagents.

The novel measuring technique may also be used for all individual measurements or series of measurements where a substrate is used up quickly, where variable quench occurs and where rapid injection of reagents is required.

Figure 6:
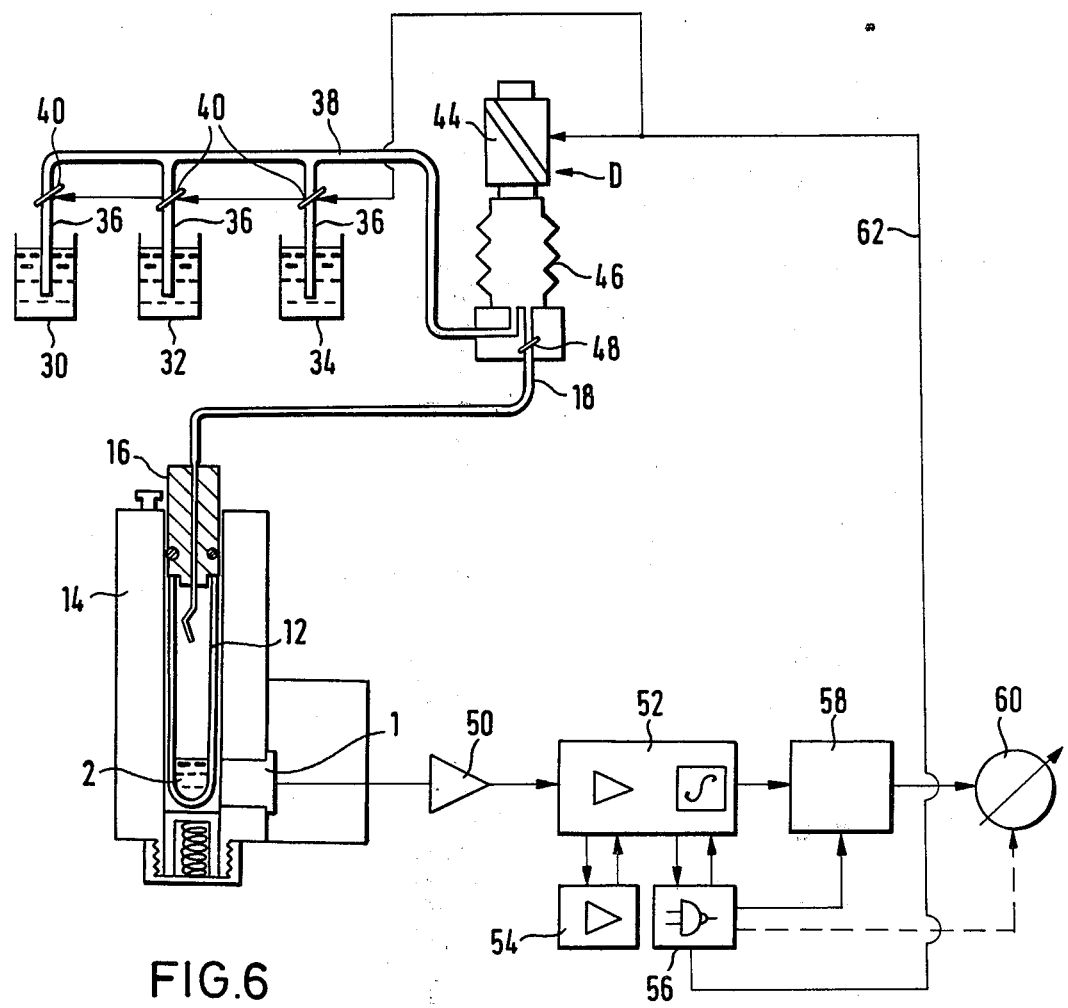
FIGS. 6 to 8 show three schematic variations of an apparatus according to the invention.

FIG. 6 is a schematic representation of an apparatus according to the invention, in which a plurality of separate reagents can be supplied via a dispenser.

According to the embodiments of FIG. 6, three different reagents can be individually contained in reservoir containers 30, 32 and 34 and can be supplied to the sample 2 disposed in a sample cuvette 12 in the darkened measuring chamber 14. The reservoir containers 30, 32 and 34 are each associated with a separate reagent extraction line 36. The reservoir containers 30, 32 and 34 are connected to a dispenser D via a common extraction line 38.

The dispenser D is preferably provided with a solenoid 44 for actuating a bellows or bellows pump 46. The bellows 46 are connected, on the one hand, with the extraction line 38 and, on the other hand, via a one-way valve 48, with an injection line 18. The injection line 18 opens via an output orifice 16 into the sample cuvette 12 disposed in the darkened measuring chamber 14. The transfer path for conveying the sample cuvettes, preferably arranged vertically with respect to the plane of the drawing, is not shown in FIG. 6.

Via a signal line, the light detector 1 is connected with an amplifier 50 which preamplifies the signal. The output of the amplifier 50 is connected with a computing and evaluating unit 52 where the measured value is processed. Zero calibration for the computing unit 52 is performed via a zero calibration unit 54. In addition, the computing unit 52 is connected with a control logic unit 56. The output signal of the computing unit 52 is connected, via a final scaling unit 58, with the output device 60.

In the schematic illustration, the control logic unit 56 acts both on the unit 58 and on the output device 60. The solenoid 44 and the one-way valves 40, provided in each one of the separate reagent extraction lines 36, are actuated via a control line 62 emanating from the control logic unit 56 and represented in FIG. 6 for reasons of simplicity as a single line but consisting preferably of individual lines which are connected with the controlled elements.

To simplify matters, let us consider here the injection of the reagent from the reservoir container 34. The control logic unit first causes the one-way valves 40 associated with the reservoir containers 30 and 32 to be closed and the one-way valve 40 of the reservoir container 34 to be opened. The preferably likewise controllable one-way valve 48, provided in the injection line 18 would also be closed. With the actuation of the solenoid subsequent to this step the appropriate reagent is sucked out of the reservoir container 34. After the one-way valve 40 to the reservoir container 34 is closed and the one-way valve 48 is opened, the reagent is injected into the sample 2 via the injection line 18 by again actuating the solenoid 40. The reaction taking place is detected via the light detector and evaluated via the computing unit 52 which in FIG. 6 contains, inter alia, an integrator, and is displayed after appropriate actuation via the control logic unit 56. A programmable microprocessor is preferably used for the evaluation of the signal.

Figure 7:
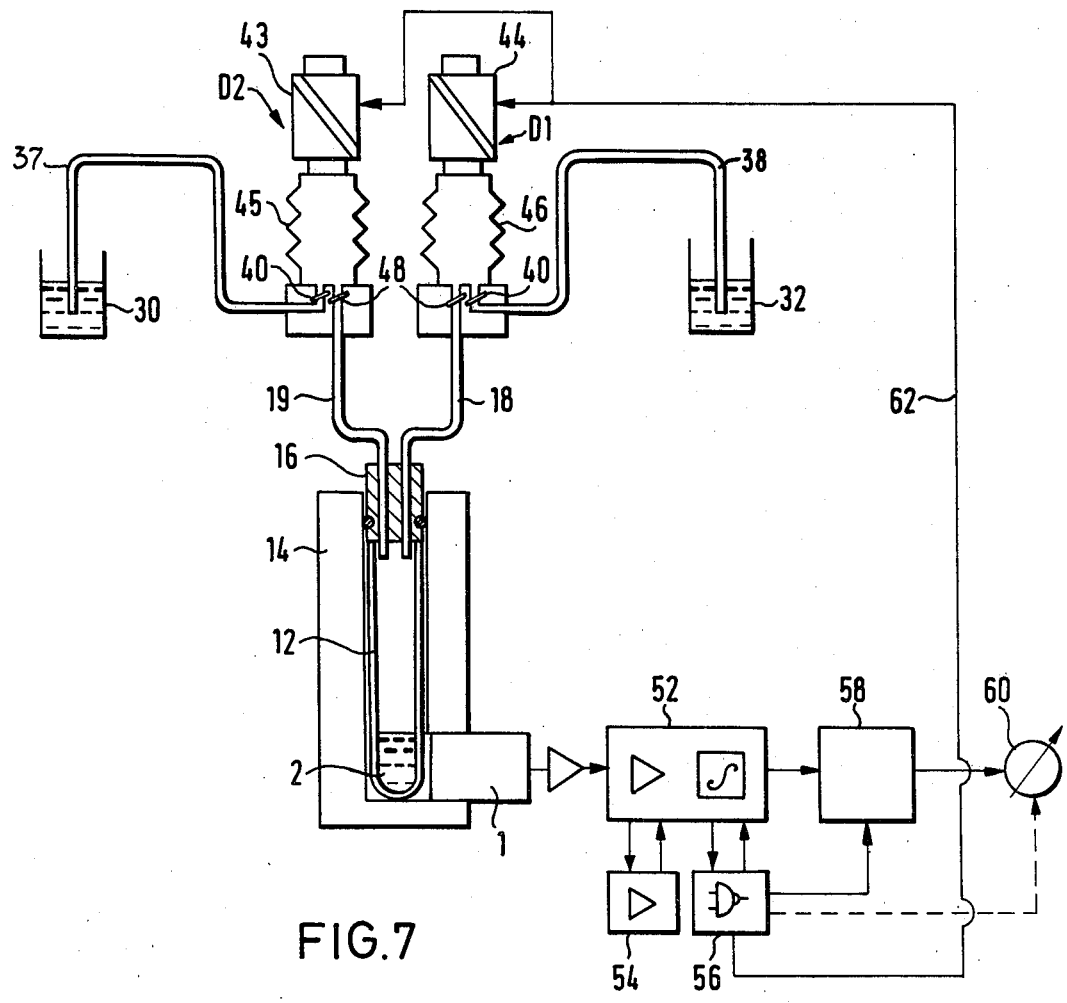

In the embodiment according to FIG. 7, the device according to the invention is provided with a separate extraction line 38 and 37 for each reagent used in the process. These extraction lines 38 and 37 are arranged at respective separate dispensers D1 and D2. The dispensers D1 and D2 each have a solenoid 44 or 43, respectively, which are connected to corresponding bellows 46 or 45.

Via separate injection lines 18 and 19, the respective dispensers D1 and D2 can inject the reagents II and I contained in the reservoir containers 32 and 30 into the sample 2. The computing and evaluating unit 52 essentially corresponds to the embodiment of FIG. 6. The control logic unit 56 in FIG. 7 actuates the solenoids 44 and 43 separately.

In the arrangement of the apparatus according to the invention shown in FIG. 7 it is possible to inject the reagents both individually, individually in succession or simultaneously once or several times into the sample 2.

Figure 8:
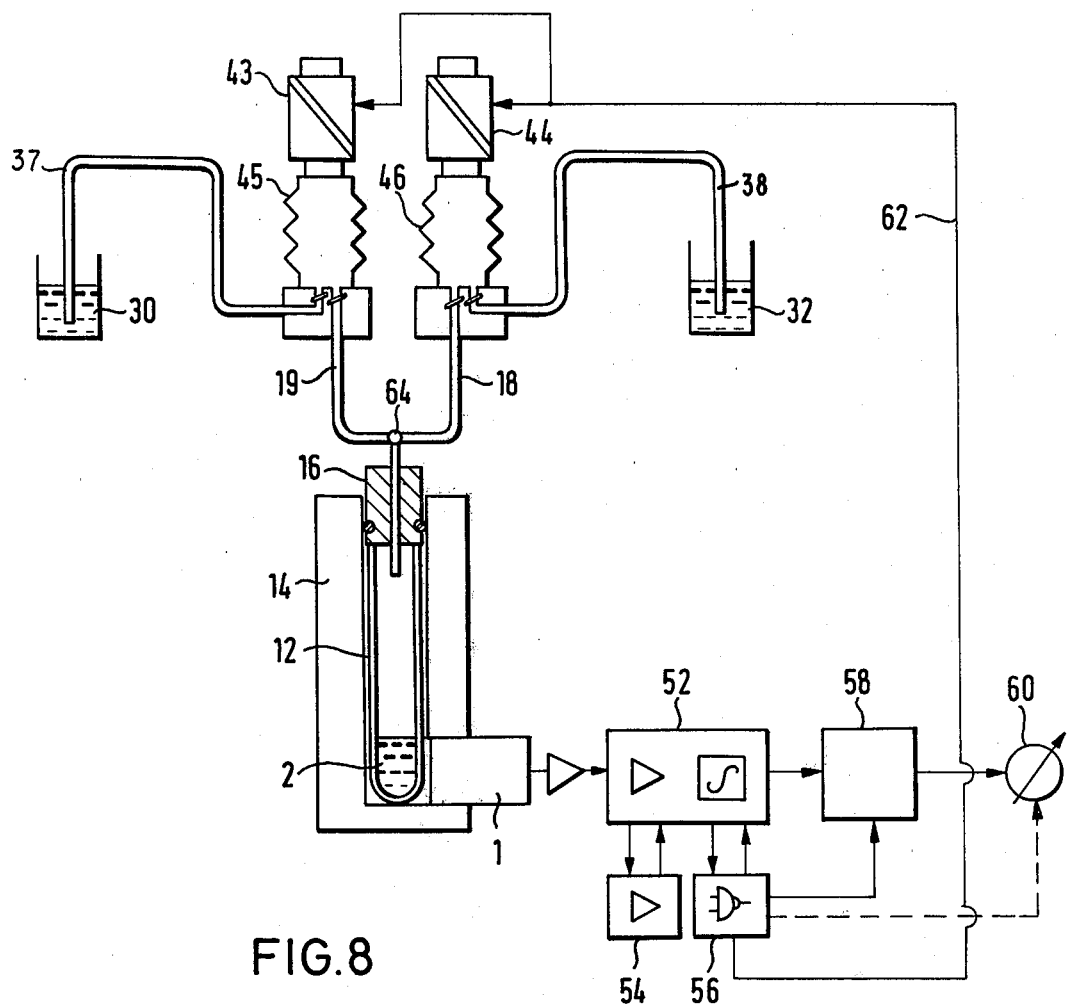

The embodiment shown in FIG. 8 essentially corresponds to that shown in FIG. 7. Instead of two injection lines which open separately into the sample cuvette 12, the injection lines 18 and 19 are here connected to a change-over valve 64 from which only one output orifice 16 leads to the sample cuvette 12. The change-over valve 64 can be put into the desired position by the control logic unit 56, for example in the manner of a three-way cock or a switch, in such a way that the process of injecting the reagents takes place in a manner similar to that in the embodiment of FIG. 7. In FIG. 8, the reagents II and I come into contact with one another, if necessary, immediately downstream of the change-over valve 64 in the output orifice 16.

We claim:

1. In a method for photometrically measuring a reaction process in which a sample has been transferred to a darkened measuring station, the sample containing an unknown quantity of a substance which acts as a reaction partner with a reagent, a first photometric measurement is taken at the darkened measuring station during the course of a reaction between a first reagent and a reaction partner which is present in the sample, and said first measurement is used for computation, the improvement comprising:

adding to the sample prior to its transfer to said darkened measuring station said first reagent;

after said first photometric measurement, adding to the sample at said darkening measuring station at least one additional reagent which is different from the first reagent, and which constitutes an additional reaction partner;

conducting a photometric measurement of the sample after the addition of each said additional reagent and during the course of a reaction between reaction partners then present in the sample; and determining from the values determined during all of the measurements, the unknown quantity of the substance present in the sample.

2. In a method for photometrically measuring a reaction process in which, at a darkened measuring station, a first reagent is added to a sample which contains an unknown quantity of a substance which acts as a reaction partner with a reagent, a first photometric measurement of the sample is conducted to measure the reaction process between the first reagent and a reaction partner which is present in the sample, and said first measurement is used for computation, the improvement comprising:

adding to the sample after said first measurement and at said darkened measuring station, at least one additional reagent which is different from said first reagent and which constitutes an additional reaction partner, conducting a photometric measurement of the sample after the addition of each said additional reagent and during the course of a reaction between reaction partners then present in the sample, and using all measurements to determine the unknown quantity of the substance present in the sample.

3. Method according to claim 1 or 2, wherein said additional reagent comprises an internal standard which is added to said sample at the darkened measuring station for the purpose of internal standardization of said sample.

4. Method according to claim 1 or 2, wherein the first measurement is approximately constant with time, and the additional reagent produces a reaction whose measurement is approximately constant with the time, but which differs from the first measurement.

5. Method according to claim 4 wherein a substrate is determined.

6. Method according to claim 1 or 2, wherein a sample is used whose first measurement shows a first maximum and wherein the additional reagent generates a second maximum in the next measurement.

7. Method according to claim 6 wherein a first curve of measured light vs. time is generated from said first maximum, the first measurement measures the first maximum, the first curve is extrapolated from said first maximum, the next measurement measures the second maximum, and the extrapolated value of the first curve at the time of measurement of the second maximum is subtracted from said second maximum, to correct for background originating from said first maximum.

8. Method according to claim 6 wherein a substrate is determined.

9. Method according to claim 1 or 2, wherein the first measurement measures a first production rate, the further reagent produces a reaction which has a second production rate different from the first production rate, and the next measurement measures the combined first and second production rates.

10. Method according to claim 9 wherein an enzyme is determined.

11. Method according to claim 1 or 2 for the measurement of bioluminescence.

12. Method according to claim 11 for the determination of ATP.

13. Method according to claim 12 wherein ATP is determined by means of firefly luminescence.

14. Method according to claim 11 for the determination of $FMNH_2$, NADH or NADPH.

15. Method according to claim 11 for the simultaneous determination of ATP, ADP and AMP.

16. Method according to claim 11 for the determination of PAPS.

17. Method according to claim 16 wherein PAPS is determined by sea-anemone bioluminescence.

18. Method according to claim 16 wherein Ca is determined by jellyfish bioluminescence.

19. Method according to claim 11 for the determination of Ca.

20. Method according to claim 11 for the determination of at least one substrate selected from the group consisting of: tRNA, creatine, glycerin, glucose-6P, GTP, cAMP by the ATP assay method, number of cells of somatic or microbial origin or the physiological activity of cells by way of measuring ATP, ADP and AMP; ethanol, D-glucose-6-P, alpha ketoglutarate, glutathione, D-lactate, and pyruvate by coupling of NADH or NADPH to a bacterial bioluminescence system.

21. Method according to claim 11 for the determination of $H_2O_2$ or superoxide, with Latia or Pholas mussel bioluminescence of with polychaeta worm bioluminescence.

22. Method according to claim 11 for the determination of creatine kinase (CK), other kinases, other enzymes which produce or consume ATP, dehydrogenases, other enzymes which produce or consume NADH or NADPH, or of oxidases, catalases or peroxidases which produce or consume peroxides or superoxides.

23. Method according to claim 22 wherein said dehydrogenase is glucose dehydrogenase.

24. Method according to claim 1 or 2 for the measurement of chemiluminescence.

25. Method according to claim 24 for the determination, with $H_2O_2$ consumption, of at least one substrate selected from the group consisting of: cholesterol, D-glucose, and uric acid.

26. Method according to claim 24 for the determination of $H_2O_2$ or superoxide with luminol, lucigenin or pyrogallol as a chemiluminescent reagent.

27. Method according to claim 1 or 2 for the measurement of fluorescence.

28. Method according to claim 27 for the determination of NADH, NADPH, DNA, RNA, amino acid, fluorescein, 4-methylumbelliferone, rhodamine or other molecules which, after having been excited with light of a certain wavelength, are capable of re-emitting fluorescent light on a different wavelength.

29. Method according to claim 1 or 2 for the measurement of light absorption.

30. Method according to claim 29 for the determination of substances which absorb light of a certain wavelength.

31. Method according to claim 30, wherein the substance being determined is NADH, NADPH or a colored substance, or a complex with an added reagent.

32. Method according to claim 31, wherein the complex with added reagent is hydrogen peroxide with diamino benzidine tetrahydrochloride or a phosphatase enzyme with 4-nitrophenol.

33. Method according to claim 1 or 2, wherein at the darkened measuring station the sample is kept at a constant temperature.

34. Method according to claim 1 or 2, wherein a "releasing agent" is added at said darkened measuring station.

35. Method according to claim 1 or 2 wherein the unknown quantity of said substance is determined according to a computer program.

36. Method according to claim 2 which is an automatic method.

37. Method according to claim 1, wherein a series of successively supplied samples are photometrically measured.

38. Method according to claim 2, wherein a series of successively supplied samples are photometrically measured.

* * * * *